(12) United States Patent
Contijoch et al.

(10) Patent No.: US 8,444,642 B2
(45) Date of Patent: May 21, 2013

(54) LAPAROSCOPIC NEPHRECTOMY DEVICE

(75) Inventors: Francisco Contijoch, Boca Raton, FL (US); Michelle Harran, Neptune City, NJ (US); Carolyn Purington, Rutland, MA (US); Tom Chen, Chino Hills, CA (US); Smita Mohan, San Jose, CA (US); Aubri Gillespie, New Preston, CT (US)

(73) Assignee: Device Evolutions, LLC, Princeton, NJ (US)

( * ) Notice: Subject to any disclaimer, the term of this patent is extended or adjusted under 35 U.S.C. 154(b) by 663 days.

(21) Appl. No.: 12/753,308

(22) Filed: Apr. 2, 2010

(65) Prior Publication Data

US 2010/0256637 A1     Oct. 7, 2010

Related U.S. Application Data

(60) Provisional application No. 61/166,345, filed on Apr. 3, 2009.

(51) Int. Cl.
 *A61B 18/14* (2006.01)

(52) U.S. Cl.
 USPC .............................. 606/51; 606/52

(58) Field of Classification Search
 USPC ......................... 606/27, 41, 51–52
 See application file for complete search history.

(56) References Cited

U.S. PATENT DOCUMENTS

| | | | |
|---|---|---|---|
| 3,938,527 A | 2/1976 | Rioux | |
| 4,516,574 A | 5/1985 | Hewes, Jr. | |
| 5,100,402 A | 3/1992 | Fan | |
| 5,156,633 A | 10/1992 | Smith | |
| 5,190,541 A | 3/1993 | Abele et al. | |
| 5,207,675 A | 5/1993 | Canady | |
| 5,304,183 A | 4/1994 | Gourlay | |
| 5,330,471 A | 7/1994 | Eggers | |
| D354,563 S | 1/1995 | Holmes et al. | |
| 5,423,814 A | 6/1995 | Zhu et al. | |
| 5,443,463 A | 8/1995 | Stern et al. | |
| 5,445,638 A | 8/1995 | Rydell et al. | |
| 5,484,435 A | 1/1996 | Fleenor et al. | |
| 5,496,333 A | 3/1996 | Sackier et al. | |
| 5,527,313 A | 6/1996 | Scott et al. | |
| 5,624,452 A | 4/1997 | Yates | |
| 5,688,269 A | 11/1997 | Newton et al. | |
| 5,776,130 A | 7/1998 | Buysse et al. | |
| 5,810,811 A | 9/1998 | Yates et al. | |
| 5,921,984 A | 7/1999 | Sutcu et al. | |
| 6,003,517 A | 12/1999 | Sheffield et al. | |
| 6,086,586 A | 7/2000 | Hooven | |
| 6,096,037 A * | 8/2000 | Mulier et al. .................. 606/49 |

(Continued)

*Primary Examiner* — Michael Peffley
*Assistant Examiner* — Daniel Fowler
(74) *Attorney, Agent, or Firm* — PatentBest; Andrew McAleavey

(57) ABSTRACT

A laparoscopic nephrectomy device is disclosed. The device has an upper jaw and a lower jaw designed to clamp a portion of an organ, such as a kidney, so as to cut off blood flow locally to a portion of that organ. The upper jaw includes a mid-jaw piece and a top jaw piece, with each piece separately articulated. The mid-jaw piece is pivotably connected to the lower jaw. A top jaw piece is pivotably connected to the mid-jaw piece. The mid-jaw and top jaw pieces include a mechanism to fix the angular orientation of the mid-jaw and top jaw pieces with respect to one another, including a retractable slide piece that is carried by the mid-jaw piece and received in a slot in the top jaw piece. The jaws have insulated troughs that carry electrode structure for applying coagulative therapies.

15 Claims, 6 Drawing Sheets

U.S. PATENT DOCUMENTS

| | | | |
|---|---|---|---|
| 6,102,909 A * | 8/2000 | Chen et al. ............... 606/45 |
| 6,126,658 A | 10/2000 | Baker |
| 6,202,914 B1 | 3/2001 | Geiste et al. |
| 6,248,062 B1 | 6/2001 | Adler et al. |
| 6,482,201 B1 | 11/2002 | Olsen et al. |
| 6,575,969 B1 | 6/2003 | Rittman, III et al. |
| 6,616,662 B2 | 9/2003 | Scholer et al. |
| 6,638,275 B1 | 10/2003 | McGaffigan et al. |
| 6,679,882 B1 | 1/2004 | Kornerup |
| 6,682,528 B2 | 1/2004 | Frazier et al. |
| 6,926,716 B2 | 8/2005 | Baker et al. |
| 6,962,589 B2 | 11/2005 | Mulier et al. |
| 6,974,453 B2 | 12/2005 | Woloszko et al. |
| 7,041,102 B2 | 5/2006 | Truckai et al. |
| 7,044,946 B2 | 5/2006 | Nahon et al. |
| 7,104,989 B2 | 9/2006 | Skarda |
| 7,115,125 B2 | 10/2006 | Nakao et al. |
| 7,184,811 B2 | 2/2007 | Phan et al. |
| 7,207,990 B2 | 4/2007 | Lands et al. |
| 7,247,155 B2 | 7/2007 | Hoey et al. |
| 7,291,161 B2 | 11/2007 | Hooven |
| 7,297,145 B2 | 11/2007 | Woloszko et al. |
| 7,312,461 B2 | 12/2007 | Lewellen et al. |
| 7,331,957 B2 | 2/2008 | Woloszko et al. |
| 7,361,172 B2 | 4/2008 | Cimino |
| 7,364,577 B2 | 4/2008 | Wham et al. |
| 7,377,920 B2 | 5/2008 | Buysse et al. |
| 7,396,356 B2 | 7/2008 | Mollenauer |
| 7,481,807 B2 | 1/2009 | Knudsen et al. |
| 7,491,201 B2 | 2/2009 | Shields et al. |
| 7,491,202 B2 | 2/2009 | Odom et al. |
| 7,500,975 B2 | 3/2009 | Cunningham et al. |
| 7,507,236 B2 | 3/2009 | Eggers et al. |
| 7,510,556 B2 | 3/2009 | Nguyen et al. |
| 7,513,898 B2 | 4/2009 | Johnson et al. |
| 7,517,347 B2 | 4/2009 | Hug et al. |
| 7,540,872 B2 | 6/2009 | Schechter et al. |
| 7,553,312 B2 | 6/2009 | Tetzlaff et al. |
| 7,572,251 B1 | 8/2009 | Davison et al. |
| 7,582,086 B2 | 9/2009 | Privitera et al. |
| 7,582,087 B2 | 9/2009 | Tetzlaff et al. |
| 7,594,916 B2 | 9/2009 | Weinberg |
| 7,597,693 B2 | 10/2009 | Garrison |
| 7,641,653 B2 | 1/2010 | Dalla Betta et al. |
| 2006/0047278 A1 * | 3/2006 | Christian et al. ............... 606/41 |
| 2007/0213712 A1 | 9/2007 | Buysse et al. |
| 2007/0225702 A1 | 9/2007 | Kaouk |
| 2007/0265616 A1 | 11/2007 | Couture et al. |
| 2008/0009860 A1 | 1/2008 | Odom |
| 2008/0033428 A1 | 2/2008 | Artale et al. |
| 2008/0045947 A1 | 2/2008 | Johnson et al. |
| 2008/0058802 A1 | 3/2008 | Couture et al. |
| 2008/0082100 A1 | 4/2008 | Orton et al. |

* cited by examiner

LAPAROSCOPIC NEPHRECTOMY DEVICE

CROSS-REFERENCE TO RELATED APPLICATIONS

This application claims priority to U.S. Provisional Patent Application No. 61/166,345, filed Apr. 3, 2009. The entire contents of that application are incorporated by reference herein in their entirety.

BACKGROUND OF THE INVENTION

1. Field of the Invention

The invention relates generally to the field of medical and surgical instruments, and more particularly to surgical instruments for manipulating and clamping the kidneys.

2. Description of Related Art

A nephrectomy is a surgical procedure in which a kidney is removed. Nephrectomies may be performed, for example, in cases of renal cell carcinoma, kidney deformity, trauma, and for live donor transplants. In a typical nephrectomy, the connections of the kidney to the renal artery and vein and to the ureter are severed and the kidney is removed. In 2008, 55,000 nephrectomies were performed, of which 50% were performed laparoscopically, i.e., through several small incisions in the abdomen, rather than by directly exposing the kidney with a large incision.

However, a full or "radical" nephrectomy is not indicated in every case. A partial nephrectomy, removal of only a portion of a kidney, may be indicated, for example, in cases in which there is a tumor in one kidney and the other kidney is functioning poorly, or in cases in which there are tumors in both kidneys. In general, partial nephrectomies may result in less morbidity, less blood loss, shorter recovery time, reduced need for pain medication, and conserved kidney function.

In a partial nephrectomy, although only a portion of the kidney is removed, the renal artery is typically clamped, cutting off blood flow to the entire kidney, not just the portion requiring removal. Once the renal artery has been clamped, the surgeon has 30 minutes to excise the tumor, restore hemostasis, and repair both the urine collection system and the defect created by the procedure. After 30 minutes, ischemia from lack of blood flow can cause tissue damage. Thus, the procedure is difficult and has a steep learning curve. Tools and procedures that allow for clamping off only an affected portion of the renal blood supply would make the partial nephrectomy easier and perhaps make the procedure more widely used.

Unfortunately, surgical tools that allow for clamping off only a portion of the renal blood supply are relatively few. As one example, U.S. Patent Application Publication No. 2004/0158286 discloses a hemostatic tissue clamp. However, most embodiments of that clamp are designed to be used only with an open surgical procedure, in which the entire kidney is exposed. Those embodiments that are designed for laparoscopic use have an extremely complex jaw mechanism.

SUMMARY OF THE INVENTION

One aspect of the invention relates to a laparoscopic nephrectomy device. The device is shaped and proportioned to be inserted through a laparoscopic port and is adapted to clamp a portion of an organ, such as a kidney, such that blood flow is interrupted locally. The end effector of the device includes a lower jaw piece and an upper jaw with two separate articulations. Specifically, a mid-jaw piece is pivotably connected with the lower jaw piece and is also coupled to a handle mechanism such that the handle mechanism can drive the upper jaw between open and closed positions. A top jaw piece is pivotably connected to the distal or forward end of the mid-jaw piece. The mid-jaw and top jaw pieces also include a mechanism for maintaining the top jaw piece in a specific angular orientation with respect to the mid-jaw piece. Specifically, the mid-jaw piece carries a slide piece that is biased forwardly by a resilient elastic member, such as a spring. The top jaw piece has a corresponding angled slot, which is sized and positioned to receive the slide piece from the mid-jaw piece. As the jaws are driven open, the slide piece pushes into the slot in the top jaw piece, locking the top jaw piece in its angular orientation with respect to the mid-jaw piece. This double articulation allows the top jaw piece to be substantially parallel with the bottom jaw piece at a specified distance, which, in turn, allows for more even pressure distribution on the renal capsule when a kidney is clamped.

The device may include electrically and thermally insulated troughs that carry electrode structure, such that the device is adapted to apply coagulative therapies, such as radiofrequency (RF) coagulative therapy, to the clamped organ or tissue.

Another aspect of the invention relates to end effectors for laparoscopic surgical instruments. The end effectors have the properties described above.

Other aspects, features, and advantages of the invention will be set forth in the description that follows.

BRIEF DESCRIPTION OF THE DRAWING FIGURES

The invention will be described with respect to the following drawing figures, in which like numerals represent like features throughout the figures, and in which.

DETAILED DESCRIPTION

Figure 1:
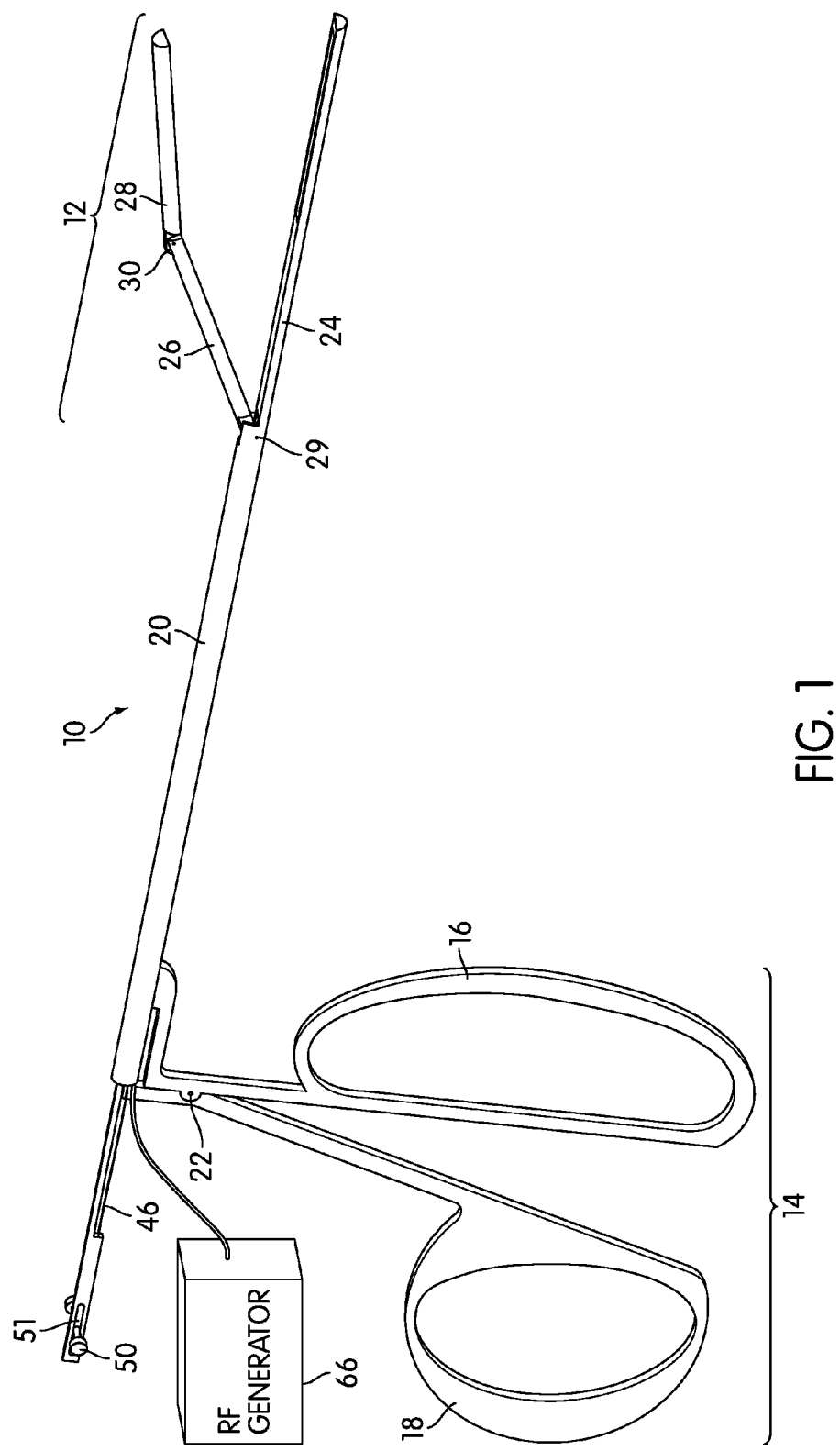
FIG. 1 is a perspective view of a laparoscopic nephrectomy device according to one embodiment of the invention.

FIG. 1 is a perspective view of a laparoscopic nephrectomy device, generally indicated at 10, according to one embodiment of the invention. The use of the device 10 in nephrectomies and partial nephrectomies will be described below; however, the device 10 need not be limited to, or used only for, those procedures.

The device 10 is an elongate instrument with an end effector 12 that is particularly adapted to clamp a portion of an organ, such as a kidney, and to apply coagulative therapies, such as radio frequency (RF) coagulation, to that organ. At the other end of the device 10, manipulating structure 14 is used by the physician or surgeon to position and actuate the end effector. Generally speaking, the device 10 is particularly adapted for use in laparoscopic surgical procedures, and to that end, the device 10 is long enough to allow the end effector 12 to be inserted into a body cavity through a laparoscopic port while the manipulating structure 14 remains outside of the body cavity, as will be described below. As shown in FIG. 1, the length of the device 10 between the manipulating structure 14 and the tip of the end effector 12 is generally cylindrical in overall shape, so as to facilitate insertion through a laparoscopic port. However, as those of skill will understand, embodiments of the invention need not be limited to laparoscopic procedures; the sizes, proportions, contours, and manipulating structure 14 of the device 10 may be modified in order to adapt the device 10 for use in open surgical procedures, if desired.

In the device 10, the manipulating structure 14 comprises a set of grips 16, 18 and associated structure. A first or stationary grip 16 is fixedly attached to a rod 20 that connects to and forms a part of the end effector 12. A second, movable grip 18 is pivotably connected to the stationary grip 16 at a grip pivot 22, so that it moves relative to the stationary grip 16. Thus, the two grips 16, 18 can be squeezed together or driven apart in a scissor-like movement.

The end effector 12 of the device 10 has two separate points of articulation in its upper jaw. A bottom jaw piece 24 arises from and comprises the distal end of the rod 20. A mid-jaw piece 26 is pivotably attached to the bottom jaw piece 24 at a first jaw pivot 29. A top jaw piece 28 is attached to the distal end of the mid-jaw piece 26 at a second jaw pivot 30. In the position shown in FIG. 1, the mid-jaw piece 26 extends at an acute angle up from the first jaw pivot 29. The jaw pieces 24, 26, 28 are generally half-cylindrical in shape, such that when the end effector 12 is closed, it also has a generally cylindrical shape. As one example of suitable proportions for the jaw pieces 24, 26, 28, the bottom jaw piece 24 may have a length of about 123 mm from its point of attachment to the mid-jaw piece 26, the mid-jaw piece 26 may have a length of about 67 mm, and the top jaw piece 28 may have a length of about 68 mm. The width of the end effector 12 and its components may be about 10 mm.

Figure 2:
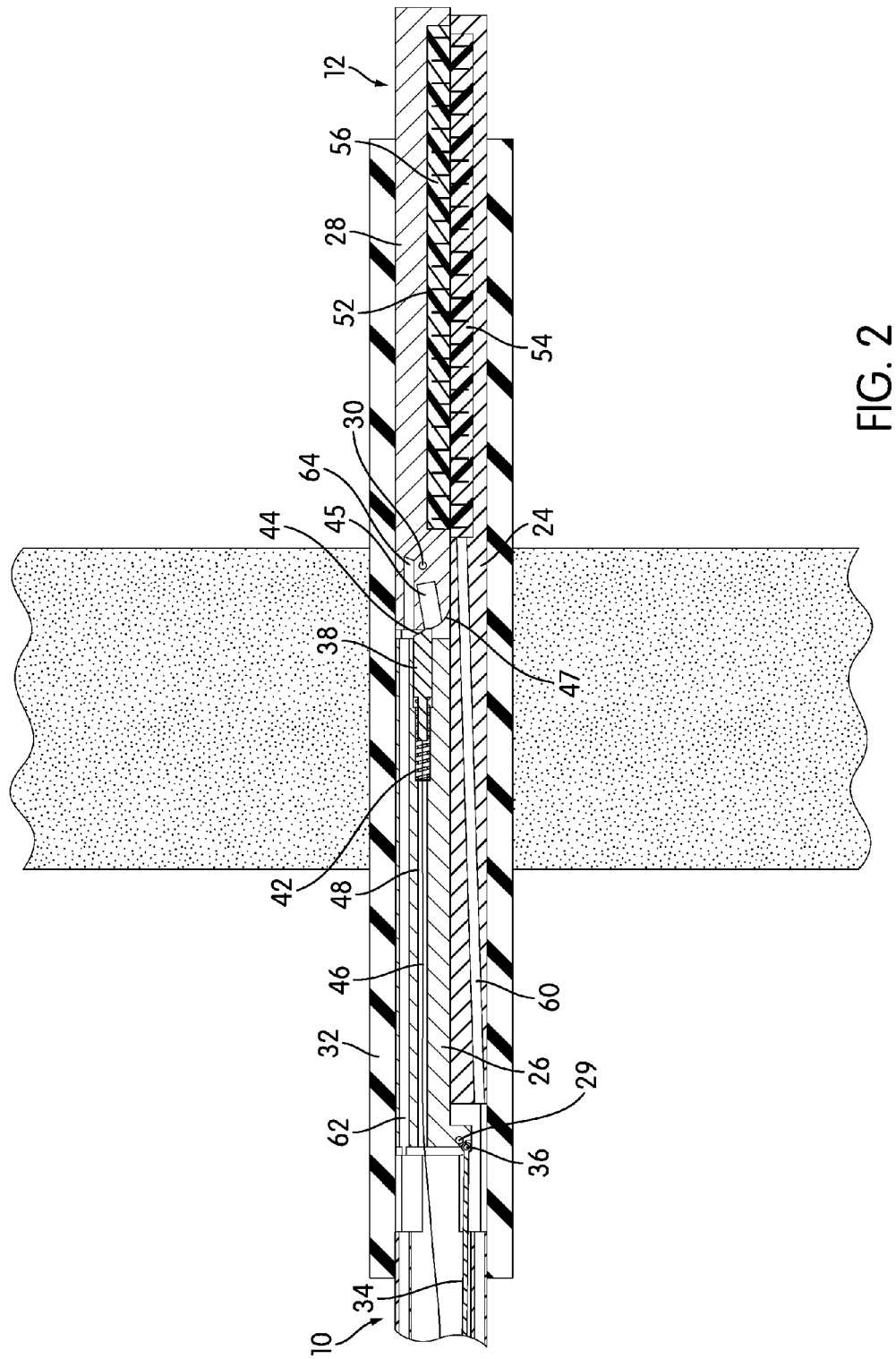
FIG. 2 is a cross-sectional view of a portion of the laparoscopic nephrectomy device of FIG. 1, shown as being inserted through a laparoscopic port.

FIG. 2 is a cross-sectional view of the device 10 being inserted through a laparoscopic port 32. The movable grip 18 is coupled to a push rod 34 that extends through the rod 20 and connects to the mid-jaw piece 26 at a push rod pivot 36. The push rod pivot 36 is just below and rearward of the first jaw pivot 29, such that when the movable grip 18 is pushed toward the fixed grip 16, the push rod 34 is pulled rearwardly and drives the mid-jaw piece 26 to rotate clockwise about the first jaw pivot 29, toward the bottom jaw piece 24. In the position shown in FIG. 2, the movable grip 18 is closed against the stationary grip 16, which maintains the end effector 12 in the position shown. Conversely, when the two grips 16, 18 are pulled apart, the push rod 34 is pushed forwardly, causing the mid jaw piece 26 to rotate counterclockwise about the first jaw pivot 29. The locations of the first jaw pivot 29 and the push rod pivot 36 are chosen so as to maximize mechanical advantage given the size constraints, which lowers the amount of force needed to open and close the end effector 12.

Figure 3:
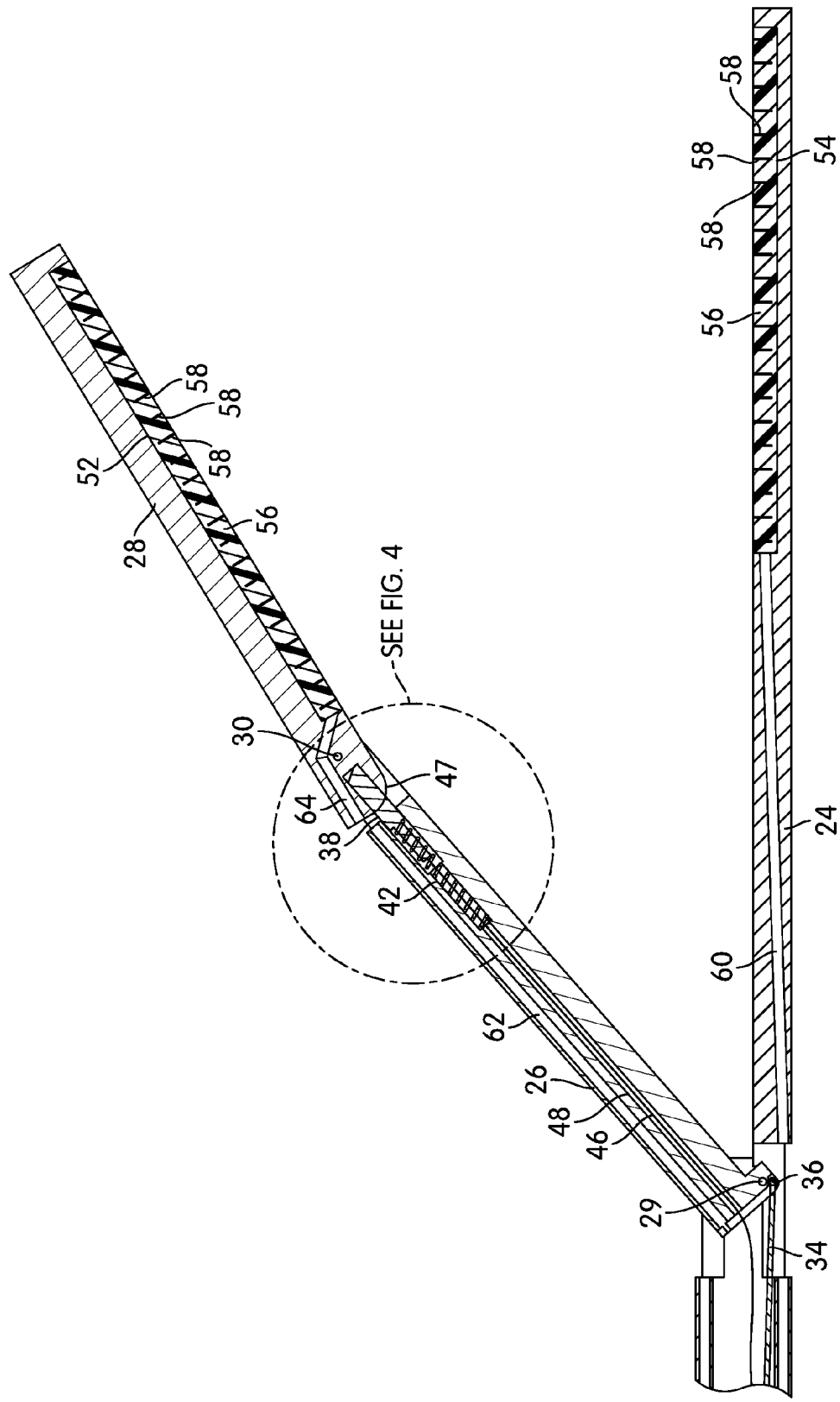
FIG. 3 is a cross-sectional view of a portion of the laparoscopic nephrectomy device of FIG. 1 with its jaw open.
Figure 4:
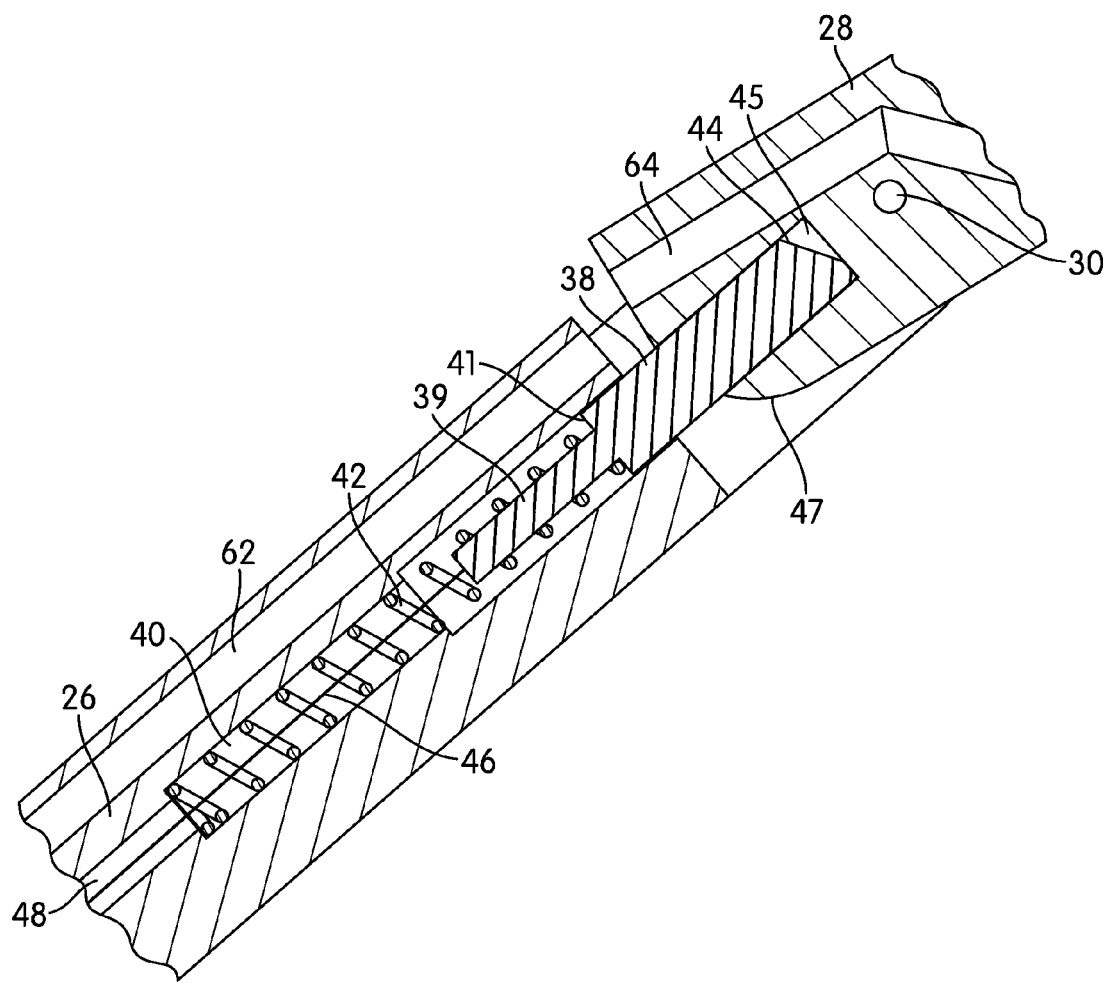
FIG. 4 is an enlarged cross-sectional view of a portion of the laparoscopic nephrectomy shown in FIG. 3.

FIGS. 3 and 4 illustrate the opening of the end effector 12 and the mechanism by which the position of the mid-jaw piece 26 and the top jaw piece 28 maintain position with respect to one another. The mid-jaw piece 26 carries a slide piece 38 within a channel 40 in the mid-jaw piece 26. A resilient elastic member 42, in this case, a compression spring, bears between the slide piece 38 and the back of the channel 40 in which the slide piece 38 rests. The resilient elastic member 42 biases the slide piece 38 forwardly.

The resilient elastic member 42 is best seen in the enlarged view of FIG. 4. More specifically, as shown in that figure, the rear portion 39 of the slide piece 38 is narrowed, and the elastic member 42 encircles it and bears against the shoulder 41 created by the narrowing of the slide piece 38.

In the fully closed position of FIG. 2, the beveled front edge 44 of the slide piece 38 rests against the proximal edge 47 of the top jaw piece 28. As the grips 16, 18 are actuated to open the end effector 12, the slide piece 38 is driven by the resilient elastic member 42 into a slot 45 in the top jaw piece 28. The beveled front edge 44 of the slide piece 38 and the rounded contour of the proximal edge 47 of the top jaw piece 28 may assist the slide piece 38 in aligning itself with the slot 45. In the illustrated embodiment, the slot 45 is angled upwardly, with an angle of 10 degrees from the horizontal. Other embodiments may use other angles, depending on the desired angular relationship between the mid-jaw piece 26 and the top jaw piece 28. When the end effector 12 is in the open position shown in FIG. 1, the slide piece 38 is in the position shown in the enlarged cross-sectional view of FIG. 4.

The angle of the mid-jaw piece 26 and the relationship of the mid-jaw piece 26 with the top jaw piece 28 allow the top jaw piece 28 and bottom jaw piece 24 to be substantially parallel to one another when the two jaw pieces 24, 28 are a specified distance apart. For example, the two jaw pieces 24, 28 may be substantially parallel to one another when they are approximately 2.5 cm apart. This allows the end effector 12 to exert more even pressure on the renal capsule when the kidney is clamped. Of course, the specified distance may vary from embodiment to embodiment and application to application. In this context, 2.5 cm is assumed to be about the jaw distance necessary to effectively clamp a portion of a kidney.

The device 10 also includes a mechanism to disengage the slide piece 38 from the slot 44, so that the end effector 12 can be returned to the position shown in FIG. 2. Specifically, a wire or pull cord 46 is connected to the proximal (rear) portion of the slide piece 38. The pull cord 46 is generally inelastic and inextensible, although it may have at least some degree of flexibility. The pull cord 46 transits the rod 20 through a channel 48 in the rod 20. At the rear of the device 10 near the manipulating structure, a transversely-extending gripping structure or cord pull 50 is connected to the cord 46 and rides in a horizontal slot 51. When the cord pull 50 is pulled back, the slide 38 is pulled out of the slot 44 by the wire 46. As the end effector 12 is closed, the slide 38 returns to the position shown in FIG. 2.

As was described briefly above, the device 10 is constructed and adapted to apply coagulative therapies to the tissue that is clamped by the end effector 12. In the illustrated embodiment, each of the top and bottom jaw pieces 24, 28 has a trough 52, 54. These troughs 52, 54 are filled with an electrically and thermally insulating material 56, such as a plastic resin. For example, a polyetherimide resin like ULTEM® 1000 polyetherimide resin may be used. Provided in or on the insulating material 56 is electrode structure 58 suitable for applying bipolar electrocautery or other forms of coagulative therapy. In the illustrated embodiment, the electrode structure 58 comprises respective pluralities of electrically conductive posts or needles. In other embodiments, the electrode structure 58 may comprise metallic strips or other similar structure, and the electrode structure in the top jaw piece 28 and bottom jaw piece 24 may differ from one another.

The bottom, mid-jaw, and top jaw pieces 24, 26, 28 include conduits or channels 60, 62, 64 that allow wires and/or other forms of electrical connecting structure to pass through the end effector 12 to connect with the electrode structure 58. (As can be appreciated from the figures, corresponding channels are provided in the rod 20, generally contiguous with the channels in the end effector 12 itself.) The wires (not shown in the figures) may be insulated or passivated as necessary. As shown in FIG. 1, the proximal end of the device 10 near the manipulating structure 14 may include a connector to connect to an RF generator 66. The RF generator 66 may, for example, apply 490 kHz energy. As those of skill in the art will realize, the connection shown between the device 10 and the RF generator 66 in FIG. 1 is schematic. The manner of connection may vary from embodiment to embodiment, based both on the specific characteristics of the device 10 and the characteristics of the RF generator 66.

Figure 5:
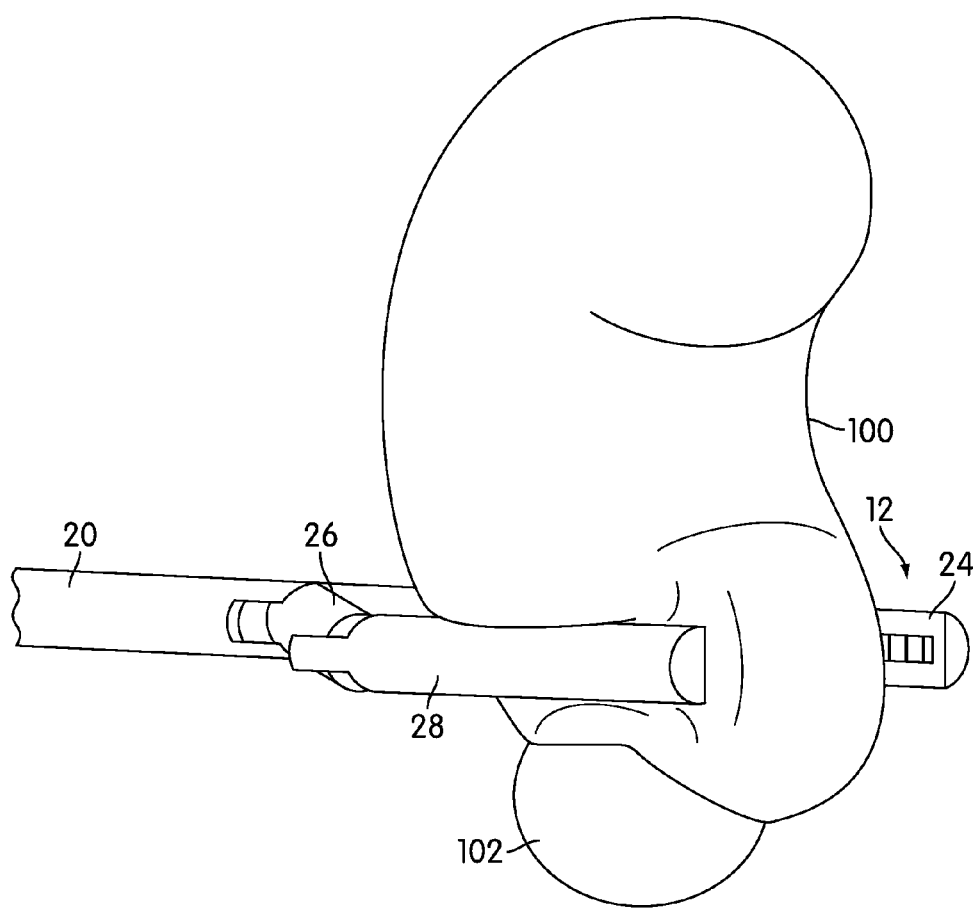
FIG. 5 is a perspective view illustrating the laparoscopic nephrectomy device of FIG. 1 in use, clamping the blood supply of a diseased portion of a kidney.
Figure 6:
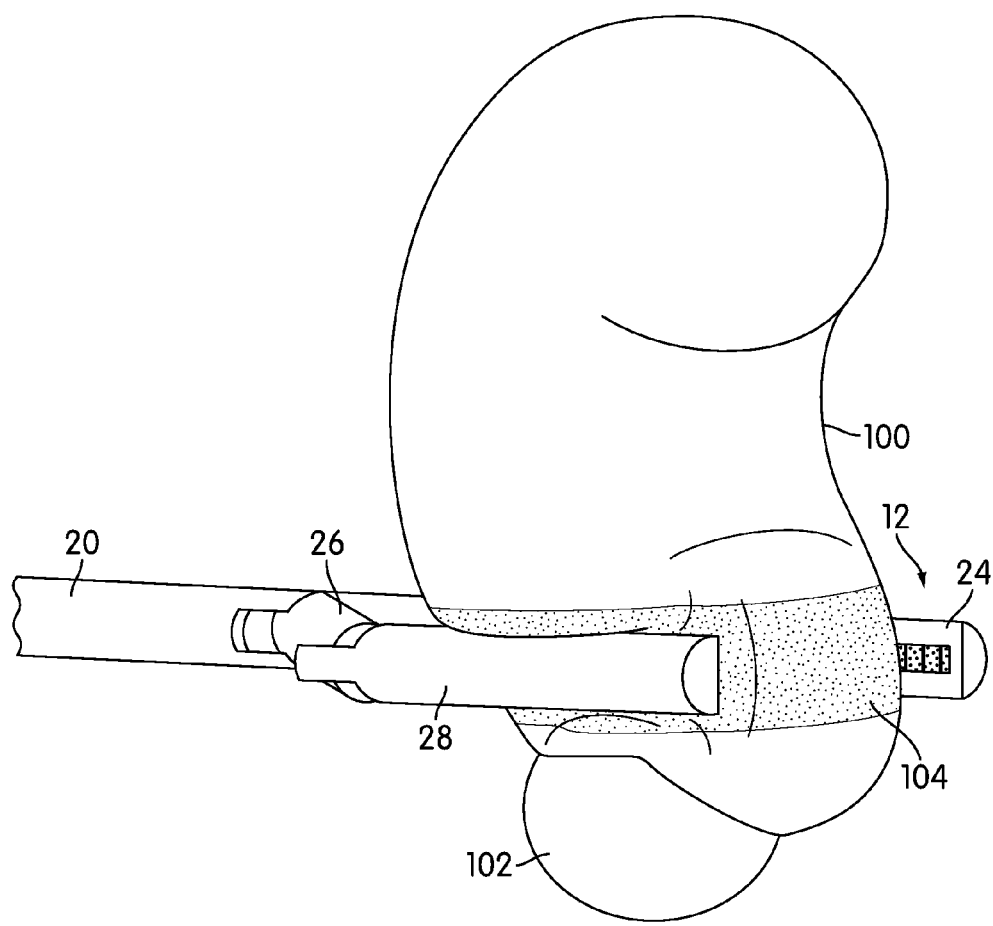
FIG. 6 is a perspective view similar to the view of FIG. 5, illustrating the kidney after using the laparoscopic nephrectomy device to apply coagulative therapy.

FIGS. 5 and 6 are perspective views of a portion of the device 10 with a kidney 100, illustrating the device 10 in use. In FIG. 5, the end effector 12 of the device 10 is clamping a kidney 100 proximate to a tumor 102. As was described above, when the end effector 12 is in the position shown in FIG. 5, the top jaw piece 28 and the bottom jaw piece 24 are substantially parallel. In some embodiments, the jaw pieces 24, 28 may have an additional layer of soft, conforming material on the faces that contact the kidney 100, so as to further reduce the force exerted on the renal capsule or to better distribute that force.

Once the end effector 12 is engaged, coagulative therapies can be applied, as shown in FIG. 6, leaving a cauterized area of tissue 104 around the end effector 12. For example, in preliminary tests with ex vivo porcine kidneys, settings of 20 watts for two minutes using a 490 kHz RF generator were found to provide adequate coagulation. In similar in vivo testing, also with porcine kidneys, 20 watts for four minutes were found to provide adequate coagulation.

As was described briefly above, the surgeon would generally apply manual force to the grips 16, 18 in order to engage the end effector 12. The locations of the pivots 29, 34 are selected so as to maximize the mechanical advantage of the device 10 and minimize the force. However, especially when coagulative therapies are being applied, it may be necessary to maintain the end effector 12 in the clamped state for an extended period of time, on the order of several minutes. In order to promote uniform application of force over time and to prevent hand cramping that might occur with long-term clamping, the manipulating structure 14 of the device 10 may include a locking mechanism for the grips 16, 18 that maintains the two grips 16, 18 in a desired position without the application of continued manual pressure. A number of these types of locking mechanisms are known in the art, and any one of these may be used.

Although FIGS. 5 and 6 show the use of the device to clamp and apply electrocoagulative therapy along a single line proximate to the renal pole, the device 10 may be used in many ways. In some procedures, it may be advantageous or necessary to clamp and coagulate in multiple places forming, e.g., a wedge shape. As those of skill in the art will realize, the device 10 may be applied multiple times in multiple places, if desired. The device 10 may also be used to provide additional or repeated coagulative therapy to the same location.

The device 10 may be made of any suitable biocompatible material, including metals, such as surgical stainless steels. Other materials, such as plastics, may be used in some embodiments, although it may be helpful if the materials that are used are autoclavable or otherwise able to be sterilized.

Although the above description focuses on the complete device 10, those of skill in the art will realize that the end effector 12 may be attached to any sort of manipulating structure, and that manipulating structure may or may not resemble the manipulating structure 14 of the illustrated embodiment. The manner in which the end effector 12 is actuated is not critical to the invention so long as it is easily and reliably used by the physician or surgeon. To that end, one advantage of the manipulating structure 14 is that it actuates the end effector 12 using familiar movements of the hands.

While the invention has been described with respect to certain embodiments, the description is intended to be exemplary, rather than limiting. Modifications and changes may be made within the scope of the invention, which is defined by the appended claims.

What is claimed is:

1. A surgical device, comprising:
   a first handle member;
   an elongate bottom jaw piece coupled to the first handle member;
   a second handle member pivotably connected to the first handle member;
   a mid-jaw piece pivotably connected to the bottom jaw piece and coupled to the second handle member such that movement of the second handle member drives the mid-jaw piece between jaw-opening and jaw-closing movements;
   a slide piece positioned and arranged for sliding movement within a channel of the mid-jaw piece;
   a resilient elastic member arranged between the slide member and the channel, the resilient elastic member being adapted to bias the slide piece forwardly; and
   a top jaw piece pivotably connected to the mid-jaw piece, the top jaw piece including a slot constructed and arranged to receive the slide piece, such that when the slide piece is engaged in the slot, the top jaw piece maintains a specified angular orientation with respect to the mid jaw piece, the specified angular orientation being such that the top jaw piece and the bottom jaw piece are substantially parallel to one another at a specified vertical distance apart.

2. The surgical device of claim 1, further comprising:
   a first insulating structure in the bottom jaw piece;
   a first electrode structure mounted in the bottom jaw piece in relation to the first insulating structure so as to be electrically insulated from the bottom jaw piece;
   a second insulating structure in the top jaw piece;
   a second electrode structure mounted on the top jaw piece in relation to the second insulating structure so as to be electrically insulated from the top jaw piece; and
   a generator electrically connected to the first and second electrode structures, the generator being adapted to apply current for bipolar electrocoagulative therapies through the first and second electrode structures.

3. The surgical device of claim 2, wherein the first and second insulating structures comprise troughs filled with an insulating material.

4. The surgical device of claim 1, wherein the slide piece has an angled front edge.

5. The surgical device of claim 1, further comprising:
   a generally inextensible cord connected to a rear portion of the slide piece, the cord extending through a channel in the surgical device toward a proximal portion thereof; and
   gripping structure connected to the cord, such that when the gripping structure is pulled rearwardly, the cord pulls the slide piece rearwardly to disengage it from the slot in the top jaw piece.

6. The surgical device of claim 1, wherein the slot is angled to the horizontal.

7. The surgical device of claim 6, wherein the slot has an angle of about 10 degrees.

8. The surgical device of claim 1, wherein the mid-jaw piece is pivotably connected to the bottom jaw piece at a first pivot that establishes a generally horizontal axis of rotation.

9. The surgical device of claim 8, further comprising a push rod coupled to the second handle member at one end and pivotably connected to the mid jaw piece at another end by means of a second pivot that establishes a second generally horizontal axis of rotation, the second pivot being spaced from the first pivot such that essentially horizontal forces exerted by the push rod on the mid-jaw piece through the second pivot cause the mid-jaw piece to rotate about the first pivot between the jaw-opening and jaw-closing positions.

10. An end effector for a surgical device, comprising:
    an elongate bottom jaw piece, the bottom jaw piece having a first insulated trough;
    first electrode structure disposed in the first trough and arranged therein so as to be electrically and thermally insulated from the bottom jaw piece;
    a mid-jaw piece pivotably connected to the bottom jaw piece, the mid-jaw piece having a second driving pivotal connection that is adapted to be connected to driving structure such that the mid-jaw piece is adapted to rotate about its pivotal connection to the bottom jaw piece between open and closed positions, the mid-jaw piece having a channel;
    a slide piece carried in the channel such that the slide piece is constructed and arranged to slide forwardly and rearwardly in the channel;
    a resilient elastic member arranged between the slide member and the channel, the resilient elastic member being adapted to bias the slide piece forwardly;
    a top jaw piece pivotably connected to the mid-jaw piece, the top jaw piece including
    a second insulated trough arranged so as to oppose the first insulated trough,
    second electrode structure disposed in the second trough and arranged therein so as to be electrically and thermally insulated from the top jaw piece, and
    a slot constructed and arranged to receive the slide piece, such that when the slide piece is engaged in the slot, the top jaw piece maintains a specified angular orientation with respect to the mid-jaw piece, the specified angular orientation being such that the top jaw piece and the bottom jaw piece are substantially parallel to one another at a specified vertical distance apart.

11. The end effector of claim 10, wherein the slide piece has an angled front edge.

12. The end effector of claim 10, further comprising a generally inextensible cord connected to a rear portion of the slide piece, the cord extending through a channel in the end effector toward a proximal portion thereof, the cord being adapted to be connected to gripping structure such that when the cord is pulled, the slide piece is disengaged from the slot.

13. The end effector of claim 10, wherein a proximal surface of the top-jaw piece that contacts the slide piece is curved.

14. The end effector of claim 10, wherein the slot is angled to the horizontal.

15. The end effector of claim 14, wherein the slot has an angle of about 10 degrees.

\* \* \* \* \*